United States Patent [19]

Messerschmidt

[11] Patent Number: 5,225,678
[45] Date of Patent: Jul. 6, 1993

[54] SPECTOSCOPIC SAMPLING ACCESSORY HAVING DUAL MEASURING AND VIEWING SYSTEMS

[75] Inventor: Robert G. Messerschmidt, Westport, Conn.

[73] Assignee: Connecticut Instrument Corporation, Philadelphia, Pa.

[21] Appl. No.: 792,195

[22] Filed: Nov. 13, 1991

[51] Int. Cl.⁵ .................... G01N 21/62; G01J 3/443
[52] U.S. Cl. .................... 250/339; 250/341; 250/353
[58] Field of Search ............ 250/339, 340, 341, 353; 356/51, 73, 326; 359/859

[56] References Cited

U.S. PATENT DOCUMENTS

| | | |
|---|---|---|
| Re. 32,912 | 4/1989 | Doyle . |
| 2,944,156 | 7/1960 | Davy et al. . |
| 3,748,015 | 7/1973 | Offner . |
| 4,473,295 | 9/1984 | Doyle . |
| 4,594,509 | 6/1986 | Simon et al. . |
| 4,633,880 | 3/1987 | Sting et al. . |
| 4,712,912 | 12/1987 | Messerschmidt . |
| 4,716,293 | 12/1987 | Harrick .................. 250/339 |
| 4,810,077 | 3/1989 | Sting . |
| 4,852,955 | 8/1989 | Doyle et al. . |
| 4,877,960 | 8/1989 | Messerschmidt et al. . |
| 4,878,747 | 11/1989 | Sting et al. . |
| 4,922,104 | 5/1990 | Eguchi et al. .......... 250/339 |
| 5,011,243 | 4/1991 | Doyle . |
| 5,015,100 | 5/1991 | Doyle . |
| 5,019,715 | 5/1991 | Sting et al. . |
| 5,106,196 | 4/1992 | Brierley . |

OTHER PUBLICATIONS

Willey, R. "FT-IR Spechophotometer for Transmittance and Diffuse Deflectance Meas. Applied Spect." vol. 30, No. 6 (1976) p. 593.
"Photometric Considerations in the Design and Use of Infrared Microscope Accessories".
Infrared Microspectroscopy, pp. 85-87.
"Mattson FTIR Quantum Infrared Miscroscope".

Primary Examiner—Paul M. Dzierzynski
Assistant Examiner—Richard Hanig

[57] ABSTRACT

A microscope accessory uses symmetrical pairs of identical parabolic mirrors as an imaging optic to map a specimen plane with a remote focus. A mask at the remote focus defines at least one measuring area for making spectroscopic measurements while a separate viewing system simultaneously provides a wide field of view of the sample at higher magnification. The sample aperture, defines as 2T sterradians of solid angle surrounding each side of the specimen plane, is multiplexed between and among different functions—such as spectroscopic measurements and visual observations. The high numerical aperture possible using identical symmetrical aberration canceling (ISAC) optics facilitates the aperture multiplexing which has particular advantage in making reflectance measurements without any need for a significant loss of throughput efficiency.

34 Claims, 8 Drawing Sheets

DIAMETER OF CIRCLE: 0.10 mm
IMAGE SEPARATION: 15 IN.
NO. OF RAYS: 2000
98.5% INSIDE CIRCLE

DIAMETER OF CIRCLE: 0.10 mm
IMAGE SEPARATION: 11 IN.
NO. OF RAYS: 2000
98.7% INSIDE CIRCLE

DIAMETER OF CIRCLE: 0.10 mm
IMAGE SEPARATION: 4 IN.
NO. OF RAYS: 2000
99.5% INSIDE CIRCLE

DIAMETER OF CIRCLE: 0.10 mm
IMAGE SEPARATION: 15 IN.
NO. OF RAYS: 2000
90.1% INSIDE CIRCLE

DIAMETER OF CIRCLE: 0.10 mm
IMAGE SEPARATION: 11 IN.
NO. OF RAYS: 2000
93.3% INSIDE CIRCLE

DIAMETER OF CIRCLE: 0.10 mm
IMAGE SEPARATION: 4 IN.
NO. OF RAYS: 2000
97.9% INSIDE CIRCLE

SPECTOSCOPIC SAMPLING ACCESSORY HAVING DUAL MEASURING AND VIEWING SYSTEMS

BACKGROUND AND SUMMARY OF THE INVENTION

Infrared spectroscopy involves two types of devices—spectrometers that generate a spectrum from infrared energy and accessories that take the infrared energy from a sample to the detector of the spectrometer. The present invention relates specifically to an accessory to deliver infrared radiant energy to a sample and to the detector of a spectrometer.

Fourier Transform—Infrared (FT-IR) spectrometers are today the spectrometers of choice for infrared spectroscopy. Whereas a dispersive spectrometer would measure one wavelength at a time, an FT-IR spectrometer measures all wavelengths at once, thus increasing the signal received by the photodetector, reducing measuring time and generally increasing efficiency. Examples of FT-IR spectrometers are well known in the art such as, for example, the Mattson Galaxy 5000. While this type of spectrometer is used in this application as an example of a suitable instrument, it is to be understood that the present invention has wide applicability beyond just FT-IR spectroscopy.

Spectroscopic analysis using radiant energy in the infrared regions of the spectrum has enormous importance independent of the particular type of spectrometer being used. Many chemical induced compounds can be identified by their distinct characteristic spectral signatures in an infrared, energy beam. Infrared spectral analysis offers a far more economical way of obtaining information than alternatives such as nuclear magnetic resonance (NMR), spectroscopy, also called magnetic resonance imaging (MRI), spectroscopy, since infrared analysis involves little more than simply shining a beam of light onto the sample. Infrared spectroscopy often works where these other, more elaborate methods do not.

Making infrared spectroscopy work, however, requires that the infrared energy first get to the sample and then get to a detector of the spectrometer. Doing this is far easier to state than to implement in practice. Infrared energy is invisible to the human eye. Selecting the sampling area therefore must be done in some indirect manner. The range of wavelengths covered by the infrared part of the spectrum is many times greater than for visible energy. There are few materials that are transmissive of infrared light and none that are equally refractive over all infrared wavelengths. Moreover, no known material can transmit all wavelengths of infrared energy equally, so any attempt to shine a beam of infrared radiant energy through a material will effectively change the wavelength distribution (color) of the beam. Accessories for infrared spectroscopy therefore usually use mirror optics since infrared lenses are impractical.

Another characteristic of infrared radiant energy is that it has a much longer wavelength than visible light. This characteristic presents a problem in that many of the things that one would want to observe using infrared energy, such as fibers, are so small that their size is comparable to that of the wavelength of the infrared energy itself. The wavelength of infrared energy defines the theoretical "diffraction limit" of what can be observed using infrared illumination. Obtaining this limit requires using optics that obtain close to the best possible resolution at infrared wavelengths.

Observing small samples using radiant energy is known as microscopy. It was perhaps natural that the first attempts to look as small things using infrared energy involved merely adopting those features of visible light microscopes that worked with infrared energy. Coates, working at the time for Perkin-Elmer, produced the first commercial infrared microscope in the late 1950's using mirror optics that, since they were composed entirely of mirrors, could be used with infrared energy without modification.

The first FT-IR spectrometers were introduced in the early 1970's. The vastly increased capabilities of FT-IR spectroscopy provoked a succession of new infrared microscopes. The second generation of microscope accessory, exemplified by the Nanospec 20-IR, adapted the original Coates design to the new generation of spectrometers. The next generation of microscope accessory, represented by the Digilab UMA 100, added the ability to analyze a microscopic area on a sample by reflecting infrared energy off its surface by splitting the aperture of a Cassegrainian mirror optic into input and output segments. An intercepting mirror was positioned as close as practical to the secondary mirror of the Cassegrainian mirror optic at a location that functioned as a "Fourier plane" to split the aperture of the microscope accessory for both reflective and infrared transmissive samples. The fourth generation of infrared microscope accessory, represented by the IR-Plan ®, shifted the intercepting mirror back from the secondary of the Cassegrainian mirror optic to an optically equivalent position. The resulting design required splitting the aperture of the Cassegrainian mirror optic only for reflective samples. A transmissive sample could be sampled using the full aperture of the microscope accessory.

The second, third and fourth generation microscope accessories proved to be successful and helped to establish the utility of microscopy in infrared spectroscopy. The inventor of the present application was an inventor of the third and fourth generation microscope accessories. See, U.S. Pat. Nos. 4,653,880, 4,877,960 and 4,878,747.

Their success and acceptance notwithstanding, all previous designs for a microscope accessory suffer from a fundamental problem. Starting with the first generation, the designers of infrared microscope accessories, including the applicant in his prior work, sought to duplicate the capabilities of existing visible light microscopes by merely using the components of a visible light microscope that worked with infrared energy. The problem with this approach is that infrared microscope accessories perform a substantially different function than do visible light microscopes. Merely duplicating a visible light microscope did not address these differences. Whereas a visible light microscope is designed to survey the widest possible field just for a given magnification, the purpose of an infrared microscope accessory is to sample a small, well defined area on the sample. Doing this with the same optics used for the visual survey is not necessary because the area of the sample to be measured spectroscopically is generally only a small section of the entire visual field of view. The result of merely duplicating visual light microscopes in a spectroscopic accessory that is over engineered, overpriced, and excessive when compared to what is needed for spectroscopic measuring of a part of a sample.

The over engineering of the infrared microscope accessory has also produced a significant problem when used in reflectance observations. Prior generations of microscope accessories performed spectroscopic measurements of samples that reflect radiant energy by dividing the aperture of a Cassegrainian mirror optic between input and output segments. This aperture division necessarily cut both the spatial resolution and throughput efficiency of the microscope accessory in half so that the available infrared energy never made it to the sample. Never was all the available energy directed to only a part of the Cassegrainian mirror optic, probably because the input pupil was circular and bringing a circular beam into only a part of the circular aperture would illuminate far too little of the aperture and reduce spatial resolution by far more than half.

Another problem with previous microscope accessories was that they all operate in either a visible inspection mode or an infrared sampling mode but never both. This false duality between visual survey of the sample and its spectroscopic analysis meant that the spectroscopist never really knew what was being measured when it was measured spectroscopically. Separating measuring from sampling also was unnatural since a microscopist would normally measure a sample while viewing it. The either/or choice between sampling and viewing, moreover, is not a function of Cassegrainian mirror optics; a single imaging optic, such as a Cassegrainian mirror optic, can be divided into different regions as shown by the previous aperture dividers used to observe reflective samples. See, for example, U.S. Pat. Nos. 4,653,880, 4,878,747, 4,915,502 and 5,011,243. There is no reason such aperture division could not extend to multiplexing visual surveying and infrared sampling provided that known steps are taken to filter out any He-Ne-laser light; it simply was not done.

There is a need in the art of FT-IR microscopy for a microscope accessory that will provide a wide field image for use in surveying a sample and a narrow field just for use in spectroscopically measuring a selected area of the sample. There is also a need to increase the spatial resolution and throughput efficiency of a microscope accessory when it is used to observe a reflecting sample. There is also a need for a microscope accessory capable of multiplexing the accessory to accommodate surveying and sampling simultaneously. None of these needs have been met in the first four generations of infrared microscope accessories discussed above.

It is an objective of the present invention to advance to a fifth generation of infrared microscope accessory that overcomes some or all of the disadvantages of previous microscope accessories. Another objective is a microscope accessory with a wide field of view for surveying a sample and a narrow field of view for measuring a selected area of that sample. Another objective is a microscope accessory that operates with substantially full spatial resolution and throughput efficiency when sampling reflective samples just as for transmissive samples. Another objective is a microscope accessory that can survey and sample simultaneously. It is also an objective of the present invention to produce a microscope accessory that is inexpensive to manufacture but that still has all the capabilities of larger, more expensive and over engineered microscope accessories.

The present invention attains these and other objectives with identical symmetrical aberration canceling optics having unitary magnification that image of a narrow field of view for making spectroscopic measurements and a separate viewing system that simultaneously provides a wide field of view of the entire sample image plane. The identical symmetrical aberration canceling mirror optics can comprise parabolic mirrors and the visual observation system can be supplied by sacrificing part of one mirror through which to view the sample image plane. The measuring and viewing systems allocate the sample aperture available to the microscope accessory, defined herein as the 2T sterradians of solid angle surrounding each side of the sample image plane, between and among the functions to be performed by the microscope accessory. Spectroscopic measurements can take place at the same time as visual observations since the separate functions occupy separate segments of the sample aperture. The identical symmetrical aberration canceling mirror optics can have a high numerical aperture to accommodate a larger portion of available sample aperture. This high numerical aperture gives the microscope accessory a measurement system with plenty of aperture to allocate between incident and reflected energy. The measurement system can measure a reflective sample without any loss of efficiency and with spatial resolution comparable to or greater than that attained with Cassegrainian mirror optics.

The present invention further facilitates confocal infrared microscopy. Masks can be positioned at remote images of the remote plane to select the area of the sample to be measured spectroscopically with the measurement system. A mirror can be positioned at one field stop to facilitate more precise sampling of transmissive samples.

These and other features of the present invention have the advantage that the high numerical aperture of the unitary focusing objectives provide diffraction-limited performance over the area needed for spectroscopic measurements and only that measuring area. The present invention actually improves resolution by increasing the numerical aperture of the measurement system using less expensive, narrow field imaging optics such as identical symmetrical parabolic mirrors rather than more expensive, wide field Cassegrainian mirror optics. The large numerical aperture allows aperture to be viewed for what it is, the full solid angle about the sample, rather than as something defined and limited by a single imaging optic. The enlarged concept of aperture provides plenty of room for multiplexing the observational and spectroscopic functions without any sacrifice in throughput efficiency. Another increase in efficiency comes from enabling viewing and sampling to happen simultaneously rather than sequentially.

All these advantages, and more, are obtained with the microscope accessory disclosed in detail below.

DETAILED DESCRIPTION

For the sake of clarity, the principles of the present invention will first be explained for schematic representations of the optical arrangement of the present invention for measuring the infrared spectrum of a sample and then for viewing a sample with visible light. Several alternative embodiments of the invention are then presented and discussed.

Infrared Measurement System

Figure 1:
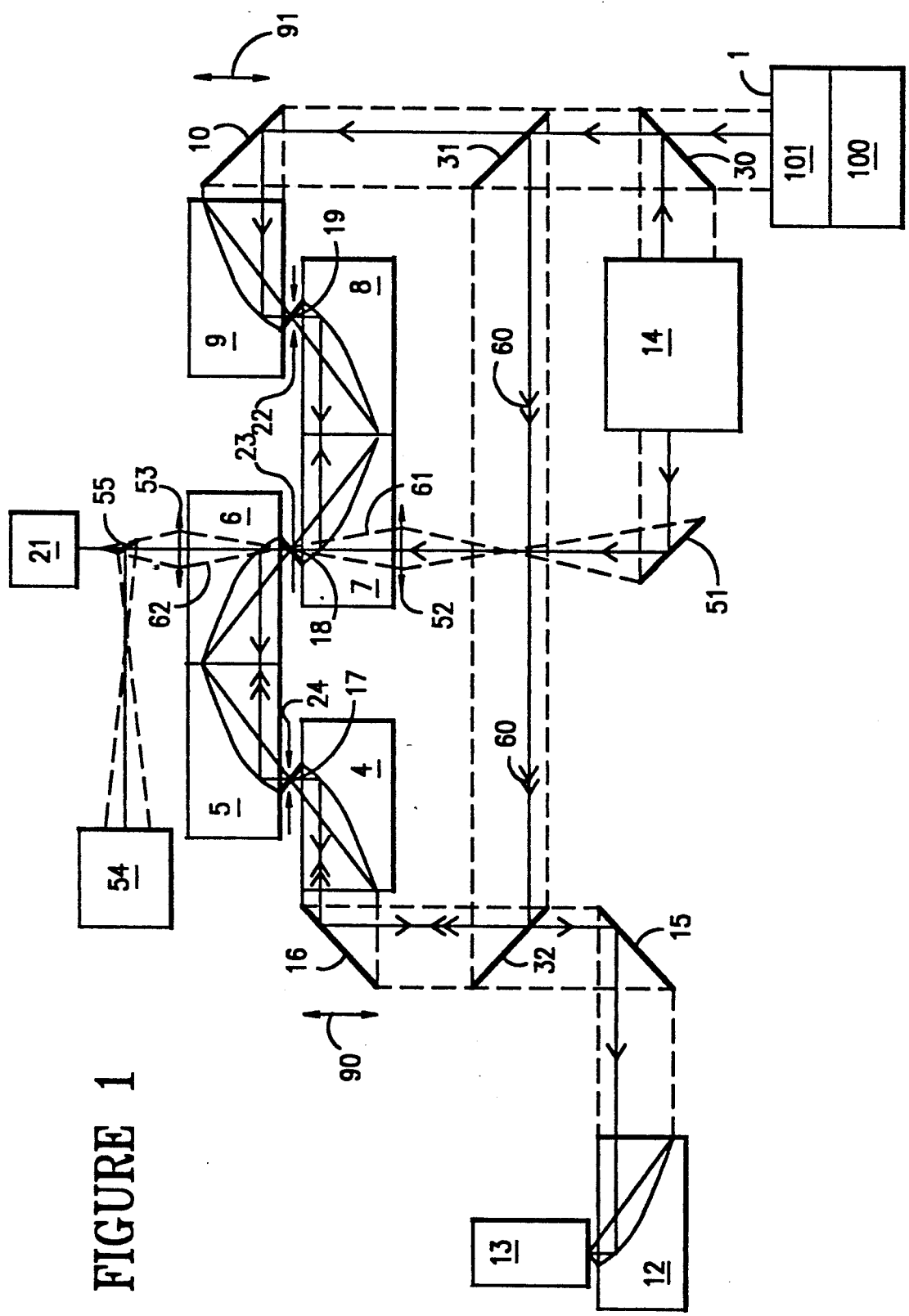
FIG. 1 is a schematic illustration of the design of a microscope accessory according to the present invention.

FIG. 1 is a schematic of the optical arrangement of a microscope accessory illustrating the principles of the present invention in the most easily comprehended manner known to the applicant. An FT-IR spectrometer 1, comprising a source of infrared energy 100 and an interferometer 101, supplies a collimated beam of infrared energy. Transfer mirror 31, shown in FIG. 1, need not be present to transmit infrared energy through a sample. The collimated beam of infrared energy from the FT-IR spectrometer 1 reaches a parabolic mirror 9 by way of a flat transfer mirror 10. The parabolic mirror 9 brings the infrared energy to a remote focus 19 where a field mask 22 can form an image that the infrared energy then projects onto a sample. Remote focus 19 eliminates aberrations that are normally present in the beam from the FT-IR spectrometer 1 and increases the energy density from the FT-IR spectrometer 1, preferably to as high a density as possible. Likewise, the mask 22 delimits the spatial extent of the infrared energy projected onto the sample, and also provides a field image which defines the magnification of the sampling system.

The radiant energy from remote focus 19 proceeds to specimen plane 23 by way of parabolic mirrors 8 and 7, respectively. The parabolic mirrors 7 and 8 form a identical symmetrical aberration canceling imaging optics having unitary magnification. The phrase "identical symmetrical aberration canceling" means that most of the aberrations introduced by one of the imaging optics are canceled by the other imaging optic. The parabolic mirrors 7, 8 bring the infrared energy to a focus 19. The foci 18, 19 are conjugate foci of the identical symmetrical aberration canceling imaging optics formed by parabolic mirrors 7, 8 enables the image of the mask 22 to be mapped with the sample image plane 23, thus ensuring that the mask 22 delimits the measuring area of the sample image plane 23 receiving the infrared energy.

Parabolic mirrors 5, 6 also form a identical symmetrical aberration canceling imaging optics having unitary magnification. Parabolic mirrors, 5, 6 map the radiant energy from the specimen plane 23 18 to a remote focus at 17. An image mask 24 is positioned at remote focus 17 to delimit the spatial extent of the infrared energy from the sample image plane 23 that is sent on to the detector. Making the remote foci 17 and 18 conjugate foci enables parabolic mirrors 5, 6 to image the specimen plane 23 onto image mask 24. Adjusting the size shape, area and relative of mask 24 to correspond to that of mask 24 enables the microscope shown in FIG. 1 to operate as a confocal microscope in which both of the masks 22 and 24 delimit the same measuring area at the specimen image plane 23.

Parabolic mirrors 4, 12 form another identical symmetrical aberration canceling imaging optics having unitary magnification of the same type as parabolic mirrors 7, 8 and 5, 6. Parabolic mirrors 4, 12 transfer the image of the mask 24 to another image at or near detector 13 by way of flat transfer mirrors 15, 16 as shown. A transfer mirror 32, shown in FIG. 1, need not be in the optical path of the infrared energy to transmit energy through the sample. Together, parabolic mirrors 4-9 comprise a transmittance measuring subsystem for obtaining the infrared spectrum of a sample positioned at the specimen plane 23.

Obtaining a spectrum from a sample that reflects infrared energy at sample image plane 23 using the microscope accessory shown in FIG. 1 can be done by inserting the two transfer mirrors 31 and 32. These mirrors deflect the infrared energy from the FT-IR spectrometer 1 to parabolic mirror 4 by way of the flat transfer mirror 16. Transfer mirrors 31 and 32 deflect the position of the infrared radiant energy beam to one side of parabolic mirror 4 by bringing the beam of infrared energy into or out of the plane of FIG. 1. The shift in the plane of propagation of the infrared energy is depicted FIG. 1 using double arrowheads 60.

Parabolic mirror 4 brings the infrared energy to the remote focus 17. Having the foci 17, 18 at a conjugate foci of the parabolic mirrors 5 and 6 ensures that the infrared energy maps an image of the mask 24 with the sample image plane 23. A reflective sample at the sample image plane 23 then reflects the radiant energy back to the parabolic mirror 6. The parabolic mirror 5 collects the reflected energy and the parabolic mirrors 5, 6 together remote focus the reflected infrared energy at the focus 17 in the general manner described above for a transmissive sample. The mask 24 delimits the measuring area at the specimen plane and the parabolic mirrors 4 and 14 also image the mask 24 at detector 13. Focus 17 and mask 24 are particularly good for use with current FT-IR spectrometers. Mask 24 also provides a useful reference for defining the magnification of the sampling system for a reflective sample. Also, the mask 24 automatically assures that the spectroscopic measurements occur in a confocal optical system.

The parabolic mirrors 4, 5 and 6 and the transfer mirrors 31,32 comprise a reflectance measuring subsystem for obtaining an infrared spectrum of a reflective sample positioned at specimen plane 23. This reflectance subsystem, like the transmittance subsystem, attains unitary magnification as defined herein. The reflectance measuring subsystem differs from the reflectance subsystem in terms of the allocation of input and output apertures as will become apparent below.

To measure a reflective sample, the reflectance subsystem for microscope accessory shown in FIG. 1 should not direct the reflected infrared energy to mirror 32. The present invention attains this result by having the reflected infrared energy fill a different part of parabolic mirror 4 than that filled by the incident infrared energy received from the FT-IR spectrometer 1. This aperture allocation, done correctly, can permit all the infrared energy from the FT-IR spectrometer 1 to reach the sample image plane 23 and be reflected back to detector 13 while still making full use of half the aperture of parabolic mirror 6. The particulars of the allocation of the aperture of the reflectance subsystem are explained in detail below.

A characteristic of the embodiment shown in FIG. 1 is that the measurement system has two input apertures, one for a sample that transmits infrared energy located at the parabolic mirror 9 and the other for a sample that reflects the infrared energy located at parabolic mirror 4. The input aperture for a reflecting sample relies on the same optic, parabolic mirror 4, used for the output aperture for a transmissive sample. This detector side aperture and sampling is considered advantageous, but does not change the description of the optical path of the radiant energy from the standpoint of path reversibility. Therefore, the measurement system is referred to herein is a single system. The components of the measuring system used for an infrared transmissive or reflective sample are what are being termed the transmittance or reflectance subsystems, respectively.

Figure 2:
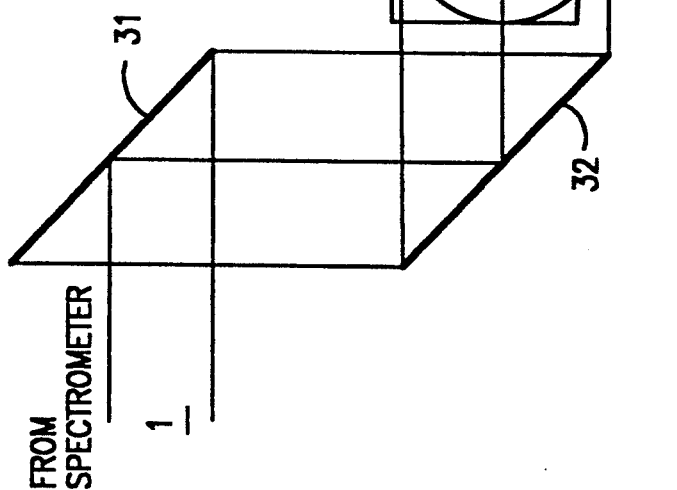
FIGS. 2 and 3 illustrate the allocation of aperture in the transmittance and reflectance subsystems, respectively, of FIG. 1.
Figure 3:
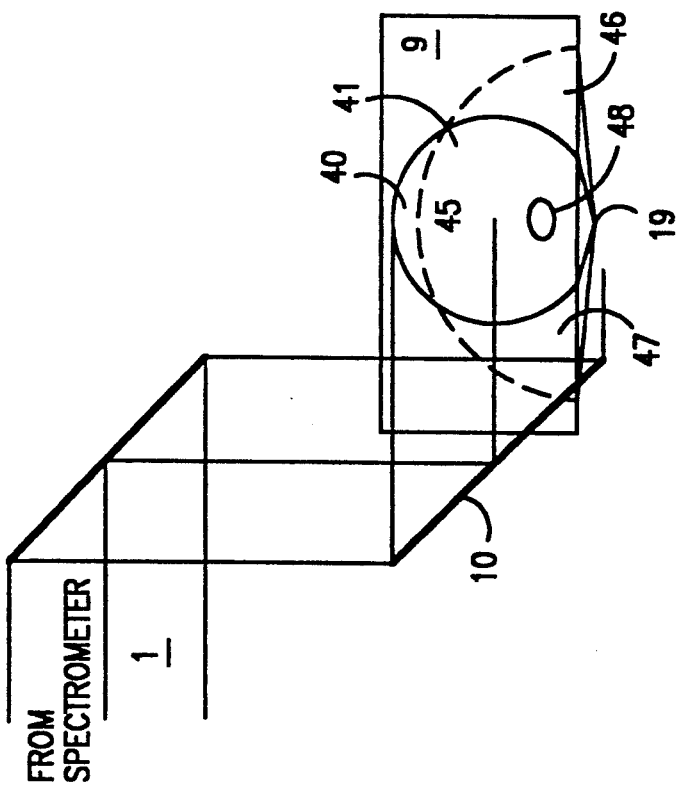

FIGS. 2 and 3 illustrate how the microscope accessory of the present invention can allocate the aperture of the measuring system for both transmissive and reflective samples. FIG. 2 shows the input for the transmittance subsystem. Infrared energy from the FT-IR spectrometer 1 reflects off the transfer mirror 10 to reach the aperture of the parabolic mirror 9. FIG. 2 shows the parabolic mirror 9 along its optical axis as having a semicircular cross section that differs in shape from the fully circular cross section of the beam of infrared energy from the FT-IR spectrometer 1. The difference in shape causes some infrared energy to be lost from the input as shown by numeral 40 in FIG. 2 and some of the input aperture to receive no infrared energy as shown by numerals 46 and 47. As shown in FIG. 2, however, most of the infrared energy falls on a segment 41 of the parabolic mirror 9 to form a new beam of infrared energy 45. It is the shape of beam 45 that defines the input aperture of the transmittance subsystem for purposes of making measurements using infrared energy.

FIG. 3 shows how the microscope accessory depicted in FIG. 1 allocates the aperture of the reflectance subsystem. The transfer mirror 32 reflects the infrared energy from the FT-IR spectrometer 1 to transfer mirror 16 where it fills region 45 on segment 41 of parabolic mirror 4. The shape of the beam 45 defines the input aperture for the reflectance subsystem. As depicted for purposes of illustration in FIG. 3, infrared energy reflected from the sample image plane 23 in FIG. 1 fills a segment 49 on parabolic mirror 9. The segment 49 is separated from the segment 41. FIG. 3 specifically depicts the reflected infrared energy as exhibiting mirror symmetry across the axis 51 of the parabolic mirror 4, it being understood that the specific shape does not matter so long as the respective areas 41 and 49 are separate on the parabolic mirror 4. The segment 49 on the parabolic mirror 4 forms an output aperture for the reflectance subsystem.

FIG. 3 shows that the input aperture 45 comprises more than half of the area of the available beam of infrared energy. This fact means that the reflectance subsystem utilizes more than the 50% of the incident energy and thus exceeds the theoretical maximum obtainable to date in microscope accessories that split the aperture of a Cassegrainian mirror optic to separate the reflected infrared energy from the incident infrared energy. The present invention attains this increased efficiency by exploiting the property that parabolic mirrors 4–9 and 12 shown in FIGS. 1 and 2 all have a very high numerical aperture. As shown in FIG. 2, the numerical aperture receiving radiant energy can be on the order of 0.8–0.95. This numerical aperture exceeds the 0.45–0.65 obtained using Cassegrainian mirror optics. Moreover, the numerical aperture of the reflectance subsystem is limited to half the maximum value attainable in the transmittance subsystem. The difference in resolution between the reflectance and transmittance subsystems is lessened because the area 48 of visual observing hole 25 in parabolic mirror 6 lies substantially in between regions 45 and 49 and thus causes little if any reduction in effective aperture for reflectance sampling whereas it is an obstruction for the transmittance subsystem.

Viewing System

A standard practice in infrared microscopy is to inspect a sample visually to select the area to be sampled using infrared energy. The present invention uses this basic technique, too, as described in detail below. However, the viewing system of the present invention represents a substantial advance over that of conventional microscope accessories.

Referring to FIG. 1, a source of visible light 14 can supply visible light to the specimen plane 23. Full field illumination for a transmissive sample can be obtained by reflecting visible light directly to the specimen plane by way of a transfer mirror 51 and a condenser lens 52. The sample image plane is then viewed in visible light using a suitable viewer 21 which could comprises any standard binocular viewer or comparable device. Holes 61 and 62 in parabolic mirrors 7 and 6, respectively, permit the visible light to reach the specimen plane 23. The image received by viewer 24 is a bright field transmissive image of the specimen plane 23. The image can have a broad and flat field of view. Such an image is ideal for inspection and identification of the area on the sample to be measured using infrared energy. Moreover, the viewing system preferably has a magnification greater than the magnification of the sampling system which, in the particular embodiment disclosed herein, has unitary magnification.

An alternative that permits broad field illumination of a reflective sample involves using a second visible light source 54 and a conventional visible light beam splitter 55. The beam splitter 55 reflects visible light from the visible light source 54 to the sample image plane 23 through the hole 62. Part of the visible light reflects off the sample at specimen plane 23, passes back through hole 62 and passes through the beam splitter 54 to the viewer 24. The image of the specimen plane 32 seen by the viewer 24 is that of a bright field reflectance image. This visible image can have the type of a broad and flat field of view that is ideal for inspection and identification of the sample. Again the viewer can have greater magnification than the sampling system.

The input aperture of the reflectance subsystem is not completely filled with infrared energy for either the transmittance or reflectance measurements. Referring specifically to FIG. 2, the two segments 46 and 47 of parabolic mirror 9 do not receive infrared energy directly from the spectrometer 1. These segments regions are therefore free to receive visible light such as that supplied by a visible light source 14. This result can be attained with a fixed mirror 30 that is shaped to correspond to the silhouette of the beam of infrared radiant energy from the FT-IR spectrometer 1. The visible light fills the segments 46 and 47 where, following a path adjacent to that of the infrared energy, the visible light can be focused by the measurement system in the same manner as the infrared energy. Any aberrations introduced by the measurement system simply do not matter at viewer 24 because the measurement system is being used as a condenser. It is well known in the literature that aberrations of a condenser in a visible light microscope do not matter much.

Since detector 13 is not responsive to visible light, there is no problem with supplying the visible light to the measurement system together with the infrared radiant energy. The viewer 21 then views the sample image plane 23 with the visible light at the same time that the detector 13 measures the spectrum of the infrared energy transmitted through sample image plane 23. The viewer 21 produces a dark field transmittance image due to the hole 61 in the parabolic mirror 7 but with good image quality over a narrow field of view centered along the optical axis of the transmittance configuration of the measurement system. For purposes of the present application, a broad field image at the sample image plane 23 has a dimension of about 2 mm.

Alternately, the visible light source 14 can supply light directly to the full aperture of parabolic 9 so as to flood the input aperture of the transmittance subsystem with visible light. Viewer 21 will still produce a dark field image, because the hole 62 in parabolic mirror 7 obstructs the light from traveling directly into the aperture of transfer optic 53. The image, however, will be more nearly bright field.

A reflective sample at sample image plane 23 can also be viewed in visible light by using the measurement system as a condenser. Visible light from the visible light source 14 can be supplied to mirrors 31, 32 and 16 along the same optical path as the infrared energy. Alternately, the visible light can follow an adjacent path by illuminating segments 46 and 47 of the parabolic mirror 4. The visible light will again be focused at the specimen plane 23 in substantially the same manner as the infrared energy. The viewer 24 forms a dark field image of the specimen plane 23 because the hole 62 obstructs the central most part of the input system.

An alternate arrangement that will produce a bright field image for viewer 24 using visible light supplied by the optics of the measurement system is to form holes 61 or 62, or both, at an angle of, for example, 5 degrees, so that visible light enters directly into the aperture of transfer optic 53. This alternative produces a visible image of specimen plane 23 that is slightly inclined which may be fully acceptable depending on the application of the microscope accessory.

Whether the visible light is supplied to the inputs of the reflectance or transmittance apertures, parabolic mirrors 4 or 9 still focus the visible light at one of the remote foci 17 or 19 where one of the masks 22 or 24 delimits it to the same area to be sampled using infrared energy. Masking the visible light means that the viewer 24 will perceive a bright spot in the field of view having exactly the same size and shape and at the same location as the area to be sampled with the infrared energy. Moreover, the viewer 24 can observe the specimen plane with visible light coming from both the measurement and viewing inputs so as to simultaneously sample and view a sample at the sample image plane 23 that is either transmissive or reflective to either the visible light or infrared energy.

To visually mask a transmissive sample requires adjusting the mask 24 to the same size, shape, area and relative position the mask 22 at the specimen plane 23. The transmittance subsystem of the present invention does this by first moving mask 22 and then adjusting mask 24 to delimit the same shape by inserting a flat mirror, not shown, just behind the mask 22 and then viewing aperture 24 can then be viewed with visible light that is transmitted through the specimen plane 23 Visible light passing through specimen plane 23 is reflected from mask plane 22 back to the specimen plane where the transfer optic 20 can image it to the viewer 21. The size, shape and relative position of mask 24 is then adjusted to delimit the same shape as mask 22 in accordance with the principles of infrared confocal microscopy. The mirror between the mask 22 and parabolic mirror 9 is then removed so that infrared sampling of the designated measuring area can proceed.

Alternative Embodiments

Figure 4:
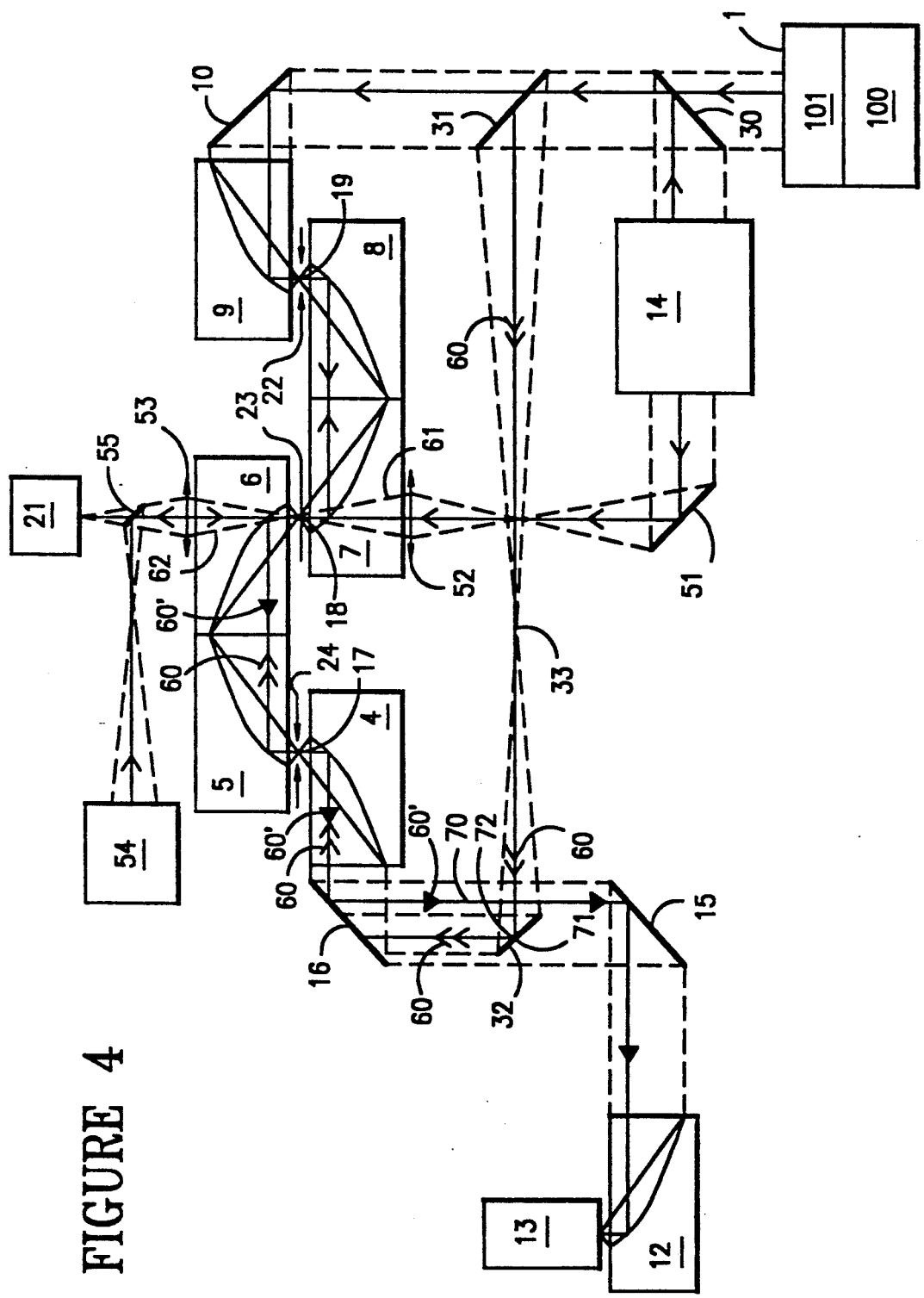
FIG. 4 shows an alternate embodiment of the present invention using a beam condenser to input infrared energy to the reflectance subsystem.

FIGS. 4 illustrates an alternate embodiment of the present invention having a reflectance subsystem with a throughput efficiency of essentially 100%. This embodiment operates in the same way as FIG. 1 for viewing the sample and for making measurements of a transmissive sample. FIG. 4 differs from FIG. 1 in that the mirrors 31 and 32 are not flat but rather are off axis parabolic mirrors of unequal focal length. The first off-axis parabolic mirror 31 focuses the infrared energy at a focus 33. The second off-axis parabolic mirror 32 collects the infrared energy from the focus 33, collimates it and directs it to the input of the reflectance subsystem at the parabolic mirror 4 by way of mirror 16.

Figure 6:
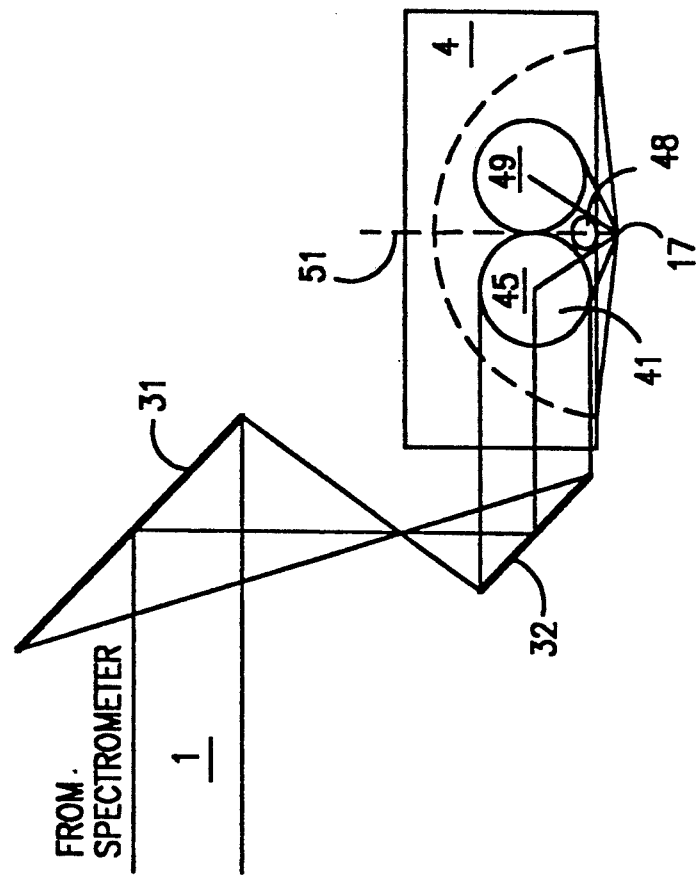
FIG. 5 and 6 illustrate the allocation of aperture for the transmittance and reflectance subsystems, respectively, of FIG. 4.
Figure 5:
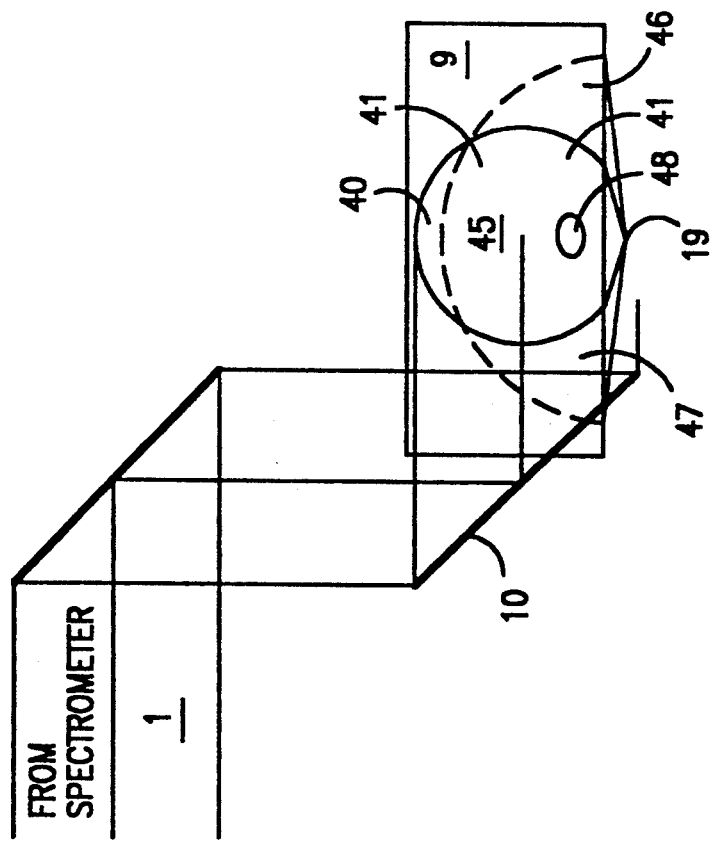

FIG. 5 shows that the input to the transmittance subsystem is the same as for the embodiment shown in FIGS. 1 and 2. FIG. 6 shows areas the input and output apertures of the reflectance subsystem 45, 49, respectively, are entirely contained within the surface of the parabolic mirror 4. Thus, substantially all of the infrared radiant energy from the FT-IR spectrometer 1 fills the input aperture 45 and substantially all the specularly reflected infrared energy returns to fill the output aperture 49 so that there is no sacrifice in throughput efficiency. The size of input aperture 45 ideally fills the maximum surface area of parabolic mirror 4 possible without crossing the axis symmetry 51 of the parabolic mirror 4.

A characteristic of the embodiment shown in FIGS. 4–6 is that parabolic mirrors 5 and 6 are antisymmetric as used in the reflectance subsystem because they are both a condenser for the incident energy and an objective for the reflected energy. A symmetric arrangement is that illustrated by the parabolic mirrors 8 and 9, 6 and 7, or 4 and 5 in FIGS. 1 and 4. Obtaining a symmetric imaging arrangement for the reflectance subsystem would require splitting the parabolic mirror 6 along its axis of symmetry (the axis 51 for the corresponding parabolic mirrors 4 and 9 in FIGS. 2, 3, 5 and 6) which would prevent using the same parabolic mirrors in both the transmittance and reflectance subsystems.

The antisymmetric positioning of the parabolic mirrors that comprise the reflectance subsystem in FIGS. 1 and 4 has an effect on filling the input and output apertures of the reflectance subsystem. Basically, if the input energy, either visible or infrared, fills most of the surface area of the parabolic mirror 4, it will do so for parabolic mirrors 5 and 6, too, since the apertures of these mirrors are mapped onto each other. The reflected energy, however, will be confined to a smaller area of the surface of the parabolic mirrors 4–6. Since the effective aperture of the reflected energy does not much matter, the antisymmetrical arrangement of the parabolic mirrors 4–6 is not believed to have any undesirable effect, and actually provides the advantage of allocating the aperture of the reflectance subsystem between the incident and reflected energy without sacrificing any part of the input energy.

FIG. 4 shows the infrared energy beam being offset from the axis of right angle rays 70. As traced through the measurement system, energy will reflect off parabolic mirror 32 at a point 72 that is not on the axis 70. This offset positioning helps to ensure that hole 62 intercepts the minimum amount of infrared energy. The distance by which the offset point 72 is displaced from axis 70 is a function of the size of the beam 71; the offset point 71 can move closer to the axis 70 as the beam 71 becomes more compressed as it leaves mirror 32.

There are other alternatives for sizing and shaping the beam of infrared energy. For example, the size of the beam of infrared radiant energy from the FT-IR spectrometer 1 can be made to equal that which is optimal for the input aperture of the reflectance subsystem. The infrared energy, and the visible light, too, could be shaped into a rectangle using a light pipe to more fully fill the input aperture of the measuring system, either the reflectance subsystem or the transmittance subsystem, or both, to enhance utilization of the aperture of the measuring system. Another embodiment, one distinctly disfavored, use mirror 32 as a conventional intercepting mirror that to divide in half the aperture of parabolic mirrors 4 and reduce the throughput efficiency of the microscope by one half in accord with the method of beam splitting used in prior infrared microscope accessories. This alternative, while possible, is disfavored since it produces both lower numerical aperture and less throughput efficiency.

The embodiments shown in FIGS. 1 and 4 both provide for masking the radiant energy from the FT-IR spectrometer 1 at two locations 22, 24. This arrangement is known as confocal microscopy and has particular advantage for FT-IR infrared spectroscopy. In reflectance mode, the aperture formed by the mask 22 can be adjusted using viewer 21 to delimit the desired measuring area at the specimen plane 23.

Figure 7:
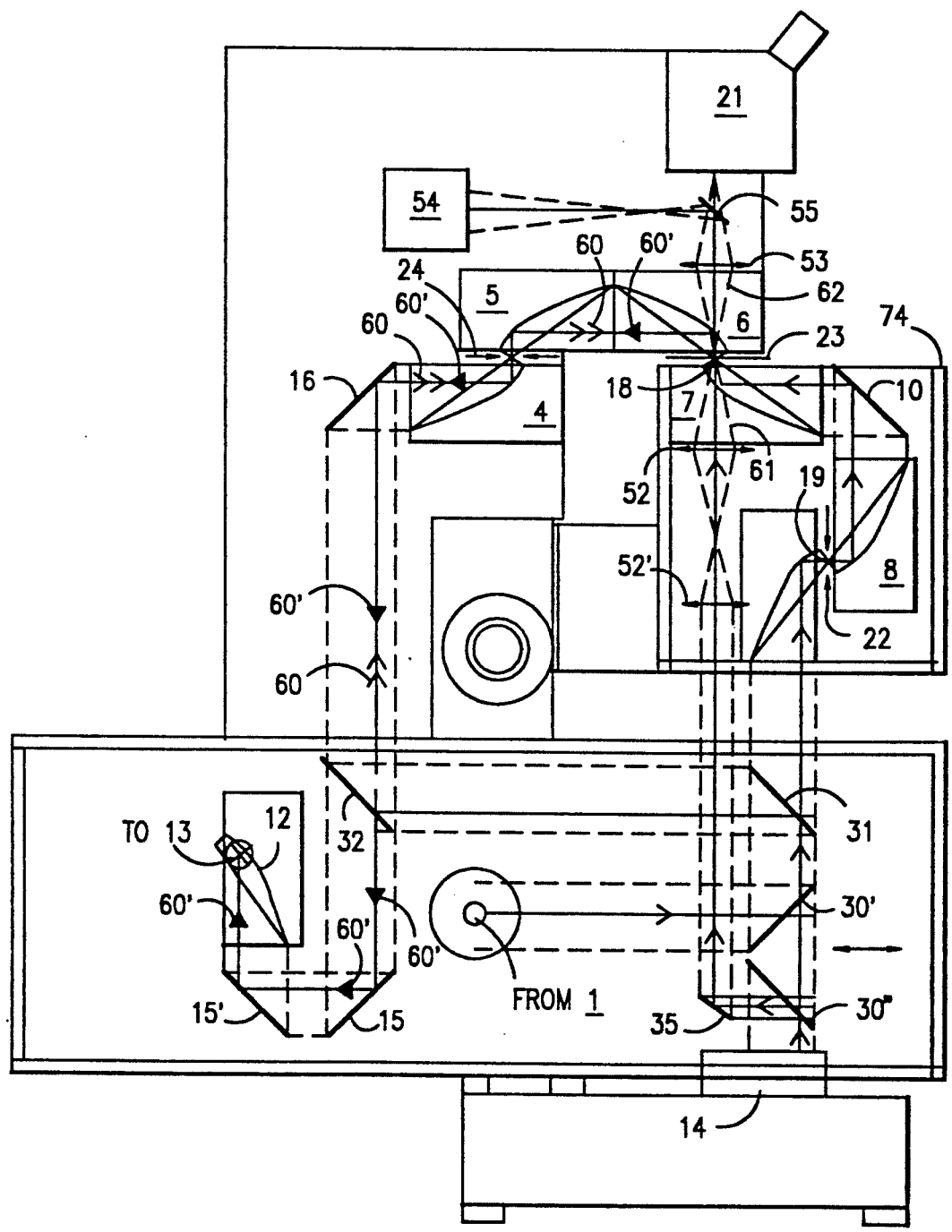
FIG. 7 shows how the design of the microscope accessory schematically illustrated in FIG. 1 can be arranged to form an actual microscope accessory.

FIG. 7 shows the schematic of FIG. 1 arranged to form something that looks like a microscope accessory. FIG. 7 differs from FIG. 1 in that the parabolic mirrors 8 and 9 have been rotated 90 degrees and the flat transfer mirror 10 has been repositioned between the parabolic mirrors 7 and 8 such that radiant energy travels directly from mirror 30 and/or visual illuminator 14 to the parabolic mirror 9. An additional mirror 15' has been added to reflect infrared radiant energy from mirrors 16 and 15 to parabolic mirror 12 which has been turned on end to direct the infrared energy to the detector 13, not shown. The FT-IR spectrometer 1, also not shown, is out of the plane of FIG. 7. The infrared energy from the FT-IR spectrometer 1 reflects off a mirror 30' to reach the input apertures of the measuring system. A mirror 30'' can direct a collimated beam of visible light to a flat transfer mirror 35 that reflects it to a condenser system comprising a pair of lenses 52, 52'. Mirrors 30' and 30'' can move back and forth as shown, separately or together, to supply visible light or infrared energy as desired. A focusing rack 74 has been added to contain the optical elements shown. As in the previous embodiments, mirrors 31 and 32 are linked to move together. The operation of the remainder of the microscope accessory illustrated in FIG. 7, is the same as previously explained for FIG. 1.

Figure 8:
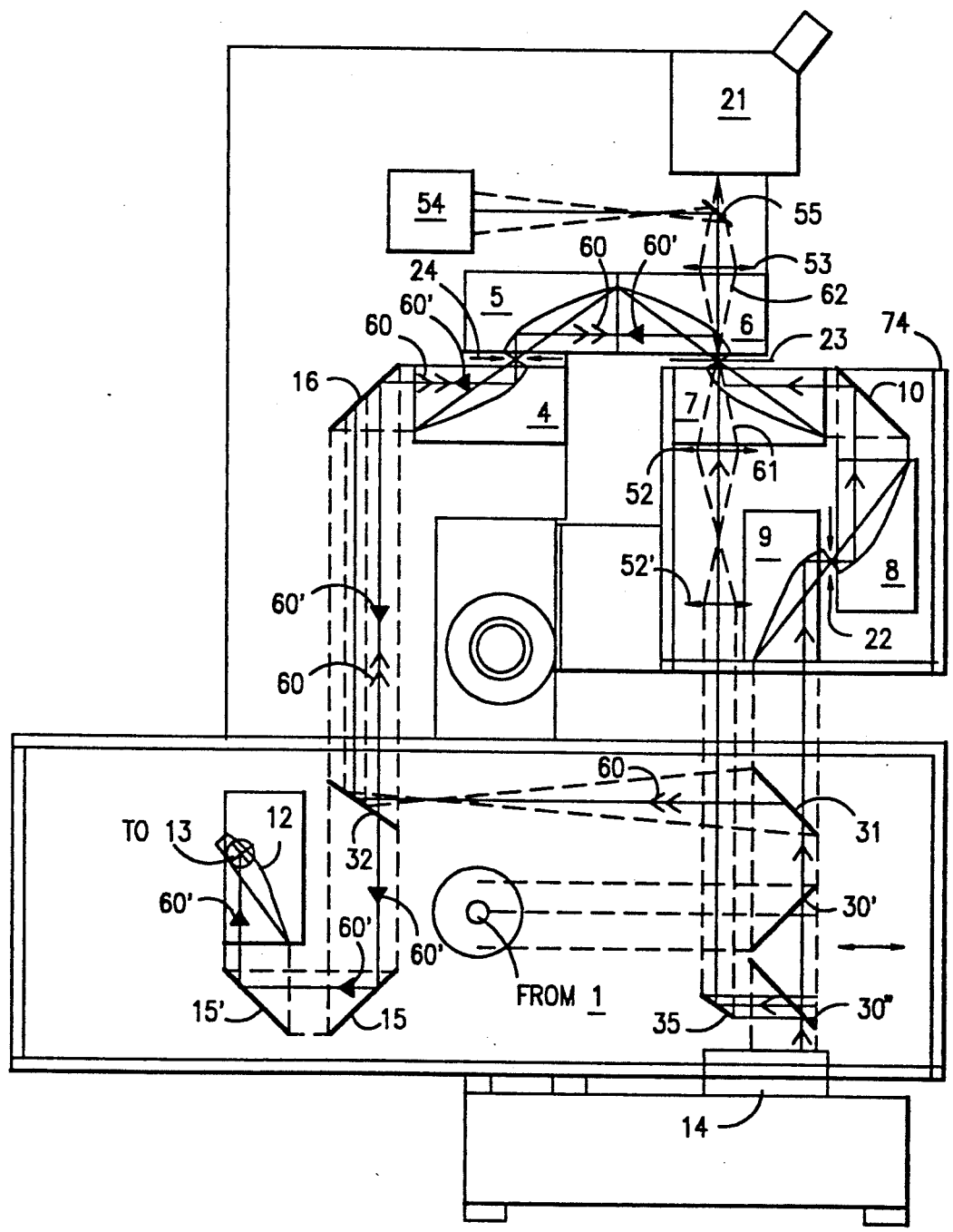
FIG. 8 shows how the design of the microscope accessory schematically illustrated in FIG. 4 can be arranged to form an actual microscope accessory.

FIG. 8 is an alternate embodiment of FIG. 7 which uses the off-axis parabolic mirrors 31, 32 described in connection with FIG. 4 above. The operation of the microscope accessory disclosed in FIG. 8 should be clear from the explanations of FIGS. 1, 4 and 7.

A feature of identical symmetrical aberration canceling mirrors parabolic mirrors 7, 8 or 5, 6 or 4, 12, is that they can provide very good image quality over a relatively narrow (e.g. 100 micron) field of view. The quality of this image does depend, however, on the separation between the symmetrical sets of paraboloids forming the identical symmetrical aberration canceling imaging optics. It is therefore desirable to keep the imaging parabolic mirrors 5–8 close together in the manner depicted in FIGS. 1 and 4.

Figure 9A:
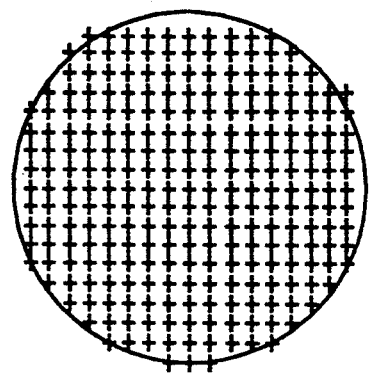
FIGS. 9A, 9B and 9C, and 10A, 10B and 10C illustrate the imaging properties of identical symmetrical parabolic mirrors.
Figure 9B:
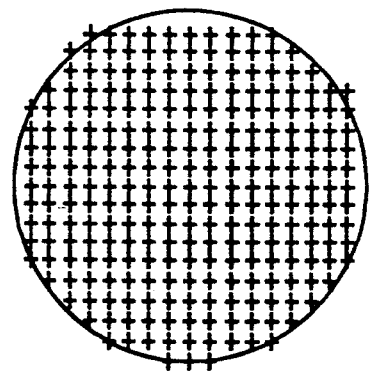
Figure 9C:
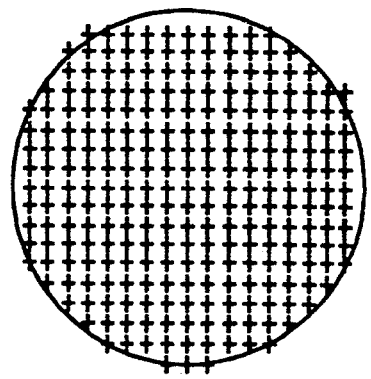

FIGS. 9 and 10 demonstrate the optical performance and image mapping properties of the identical symmetrical parabolic mirrors shown in FIGS. 1–8. FIG. 9 shows the imaging properties for a 10 micron circle with a symmetrical sets of identical parabolic mirrors having essentially a 3" diameter half circle aperture Separating the paraboloids by 15 inches still leaves 98.5% of the rays starting within the 10 micron circle being imaged within the same circle. The percentage increases to 98.7% for a separation of 11 inches and 99.5% for a separation of four inches as shown in FIGS. 9B and 9C, respectively.

Figure 10A:
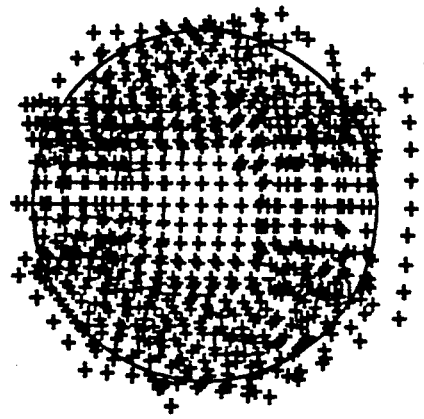
Figure 10B:
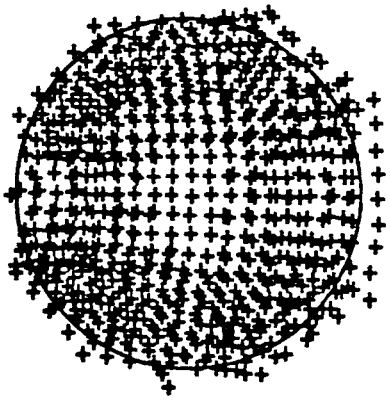
Figure 10C:
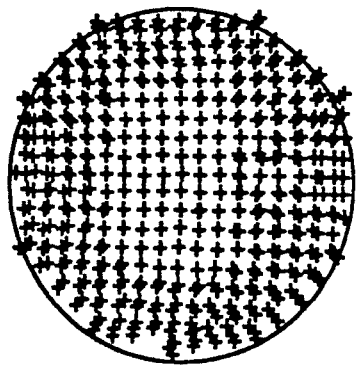

FIG. 10 illustrates the field of view of the measuring system for the optics used in the foregoing embodiment to image the measuring area. FIG. 10A shows that separating the 3" diameter parabolic mirrors in FIG. 9 by 15" while imaging a 100 micron spot causes almost 10% of the rays starting within the circle to be imaged outside the circle. The performance improves to 93.3% for a separation of 11 inches and 97.9% imaged within the circle for a separation of four inches shown in FIGS. 10B and 10C respectively. The optical performance degrades even more with greater separation between the mirrors on larger diameter measuring areas. The right quality of the identical symmetrical aberration canceling imaging optics thus does not extend substantially beyond the measuring area, nor need it since, for a spectroscopic accessory, there is no need for a wide, flat field image beyond the measuring area and the identical symmetrical aberration canceling imaging optics are completely capable of projecting the masked sampled area onto a centrally selected region for spectroscopic analysis without significant optical distortion. Thus, the present invention avoids the over engineering that so plagued previous generations of microscopic accessories, and does so by utilizing sampling optics optimally designed to sample the thing being spectroscopically measured.

Referring back to FIG. 1, the present invention multiplexes the sample aperture around the specimen plane 23 with the viewing system comprising, inter alia, the lenses 52, 53 and the viewer 21, and the measuring system defined above as including the parabolic mirrors 4–9. There is no reason why the aperture of a single imaging optic could not be allocated between sampling and viewing systems by, for example, using a mask positioned at or near a Fourier plane of the single imaging optic. The use of separate optical systems for viewing and sampling, as illustrated herein, has the advantage that each system can be engineered to have the optical performance needed for its assigned task, e.g., viewing and sampling, so as to avoid over engineering the microscope accessory.

The principles, preferred embodiments and modes of operation of the present invention have been set forth in the foregoing specification. The embodiments disclosed herein should be interpreted as illustrative and not as restrictive. The foregoing disclosure is not intended to limit the range of equivalent structure available to a person of ordinary skill in the art in any way, but rather to expand the range of equivalent structures in ways not previously thought of. Numerous variations and changes can be made to the foregoing illustrative embodiments without departing from the scope and spirit of the present invention as set forth in the appended claims.

What is claimed is:

1. A microspectrometer accessory, comprising:
    a viewing system occupying a first segment of a sample aperture, the viewing system projecting an image of an observation area of a specimen plane to a remote visual image at a viewing magnification, and
    a spectroscopic measuring system occupying a second segment of the sample aperture that is separate from the first segment, the spectroscopic measuring system comprising at least a first set of identical symmetrical aberration canceling imaging mirror optics that map the specimen plane with at least a first remote focus, the specimen plane including a measuring area, the spectroscopic measuring system having a specimen magnification that is less than the viewing magnification, and the measuring area being smaller than the observation area.

2. A microspectrometer accessory as claimed in claim 1, wherein the spectroscopic measuring system comprises:
    a reflectance subsystem in which the spectroscopic measuring system maps the specimen plane with the remote focus, and
    a transmittance subsystem in which the spectroscopic measuring system maps a second remote focus with the specimen plane.

3. A microspectrometer accessory as claimed in claim 1, further comprising at least a first mask positioned at the remote focus to delimit the measuring area.

4. A microspectrometer accessory as claimed in claim 2, wherein the spectroscopic measuring system has a numerical aperture at the specimen plane in the range of 0.8 –0.95.

5. A microspectrometer accessory as claimed in claim 2, further comprising a second mask at the second remote focus.

6. A microspectrometer accessory as claimed in claim 2, wherein the reflectance and transmittance subsystems share at least a part of a common output aperture.

7. A microspectrometer accessory as claimed in claim 1, wherein the first set of identical symmetrical aberration canceling imaging mirror optics comprise parabolic mirrors.

8. A microspectrometer accessory as claimed in claim 2, wherein both the reflectance and transmission subsystems comprise at least first and second pairs of identical symmetrical aberration canceling imaging mirror optics.

9. A microspectrometer accessory as claimed in claim 1, wherein
    the spectroscopic measuring system comprises a transmission subsystem which includes the first set of identical symmetrical aberration canceling imaging mirror optics and a second st of identical symmetrical aberration canceling imaging mirror optics, the transmission subsystem transmitting radiant energy through the specimen plane, the second set of identical symmetrical aberration canceling imaging mirror optics forming a second remote focus, and the first set of identical symmetrical aberration canceling imaging mirror optics having a first hole through which visible light form the specimen plane can pass,
    the spectroscopic measuring system further comprising at least one mask at least one of the first or second remote foci,
    the spectroscopic measuring system further comprising a reflectance subsystem which includes the first set of identical symmetrical aberration canceling imaging mirror optics, the reflectance subsystem multiplexing incident and reflected radiant energy by having half of a beam of each occupy separate segments of the first set in a reflectance mode, and
    the viewing system comprises a binocular viewer which receives the visible light via the first hole in the first set of identical symmetrical aberration canceling imaging mirror optics.

10. A microspectrometer accessory as claimed in claim 9, wherein the hole in the first set of identical symmetrical aberration canceling imaging mirror optics forms less than a right angle with the specimen plane.

11. A microspectrometer accessory as claimed in claim 10, wherein the hole forms an angle of 5 degrees with respect to a right angle with the specimen plane.

12. A method of spectroscopic measuring which involves mapping a specimen plane with a remote focus, comprising:
    supplying more than half of a beam of radiant energy to a first segment of an aperture of an imaging mirror optic, the imaging mirror optic focusing the more than half of the beam of radiant energy at a specimen plane,
    collecting most of any radiant energy that is specularly reflected from the specimen plane using a second segment of the aperture of the imaging mirror optic, the second segment being separate from the first segment, and
    directing substantially all of the reflected radiant energy, as collected, to a detector to produce a spectrum.

13. A method of spectroscopic measuring as claimed in claim 12, wherein the radiant energy is infrared radiant energy.

14. A method of spectroscopic measuring as claimed in claim 12, wherein substantially an entire beam of radiant energy is supplied to the first segment.

15. A method of spectroscopic measuring as claimed in claim 12, wherein the imaging mirror optic comprises identical symmetrical aberration canceling imaging mirrors.

16. A method of spectroscopic measuring as claimed in claim 13, further comprising producing a spectrum from the infrared radiant energy.

17. A method of spectroscopic measuring as claimed in claim 15, wherein the first or second segments are large enough to give the imaging mirror optic a numerical aperture in the range of 0.8–0.95.

18. An accessory for multiplexing spectroscopic measuring using a spectrometer, comprising:

an imaging mirror objective having an input aperture, an output aperture and mapping a remote focus at a specimen plane with at least one remote focus, a supply of a first type of radiant energy to a first segment of the input aperture, a first optical system occupying a first segment of the output aperture, a second optical system occupying a second segment of the output aperture that is separate from the first segment, and a detector for the spectrometer, the detector being a part of at least one of the optical systems.

19. An accessory for multiplexing spectroscopic measuring as claimed in claim 18, wherein the mirror objective comprises identical symmetrical aberration canceling imaging mirrors.

20. An accessory for multiplexing spectroscopic measuring as claimed in claim 18, further comprising a supply of a second type of radiant energy to a second segment of the input aperture that is separate from the first segment of the input aperture.

21. An accessory for multiplexing spectroscopic measuring as claimed in claim 20, wherein the mirror objective comprises identical symmetrical aberration canceling imaging mirrors.

22. An accessory for multiplexing spectroscopic measuring as claimed in claim 18, wherein at least one of the first or second optical systems supplies at least one of the types of radiant energy to the detector for an infrared spectrometer.

23. An accessory for multiplexing spectroscopic measuring using a spectrometer, comprising:

a imaging mirror objective having an input aperture, an output aperture and mapping a specimen plane with at least one remote focus, a supply of a first type of radiant energy to a first segment of the input aperture, a supply of a second type of radiant energy to a second segment of the input aperture that is separated from the first segment, a first optical system occupying a first segment of the output aperture, and a detector for the spectrometer, the detector being a part of at least the first optical system.

24. An accessory for multiplexing spectroscopic measuring as claimed in claim 23, wherein the mirror imaging objective comprises identical symmetrical aberration canceling imaging mirrors.

25. An accessory for multiplexing spectroscopic measuring as claimed in claim 23, wherein the detector is for an infrared spectrometer.

26. An accessory for multiplexing spectroscopic measuring using a spectrometer, comprising at least one set of identical symmetrical aberration canceling imaging mirrors having an aperture that occupies at least a segment of a sample aperture about a sample, the one set of identical symmetrical aberration canceling imaging mirrors mapping a remote focus with a specimen plane, the identical symmetrical imaging mirrors having first and second segments, the first segment being separate from the second segment, a supply of more than half of a beam of radiant energy to the first segment, and an output which directs from the second segment substantially all of the radiant energy from the first segment that is specularly reflected at the specimen plane to a detector for a spectrometer.

27. An accessory for multiplexing spectroscopic measuring as claimed in claim 26, wherein the identical symmetrical aberration canceling imaging mirrors have at least a third segment which receives at least a second beam of radiant energy, the third segment being separate from the first and second segments.

28. An accessory for multiplexing spectroscopic measuring as claimed in claim 27, wherein the first beam of radiant energy comprises infrared energy and the second beam of radiant energy comprises visible light.

29. A method of multiplexing spectroscopic measuring using a spectrometer, the spectrometer having a detector, an input aperture, an output aperture and at least one imaging mirror optic, comprising imaging the input aperture with the output aperture by mapping a focus at a specimen plane with at least one remote focus, supplying a first type of radiant energy to a first segment o the input aperture, delimiting a measuring area on the specimen plane at the remote focus using the first type of radiant energy, supplying a first type of radiant energy from the specimen plane to a first segment of the output aperture, simultaneously supplying the first type of radiant energy from the specimen plane to a second segment of the output aperture that is separate from the first segment, and directing the first type of radiant energy from at least one of the segments of the output aperture to the detector.

30. A method of multiplexing spectroscopic measuring as claimed in claim 29, further comprising producing an infrared spectrum.

31. A method of multiplexing spectroscopic measuring as claimed in claim 29, further comprising simultaneously supplying a second type of radiant energy to a second segment of the input aperture, and simultaneously delimiting the measuring area on the specimen plane at the remote focus using the second type of radiant energy.

32. A method of multiplexing spectroscopic measuring as claimed in claim 31, further comprising obtaining an infrared spectrum of at least one type of radiant energy from at least one of the segments of the output aperture.

33. A method of multiplexing spectroscopic measuring using a spectrometer, the spectrometer having a detector, an input aperture, an output aperture and at least one imaging mirror optic, comprising imaging an input aperture with an output aperture by mapping a focus at a specimen plane with at least one remote focus, supplying a first type of radiant energy to a first segment of the input aperture, delimiting the measuring area on the specimen plane at the remote focus using the first type of radiant energy, simultaneously supplying a second type of radiant energy to a second segment of the input aperture that is separate from the first segment, simultaneously delimiting the measuring area on the specimen plane at the remote focus using the second type of radiant energy, and supplying one of the first or second types of radiant energy from the specimen plane to the detector by way of a first segment of the output aperture.

34. A method of multiplexing spectroscopic measuring as claimed in claim 33, further comprising obtaining an infrared spectrum.

* * * * *